(12) United States Patent
Shiau et al.

(10) Patent No.: US 6,585,392 B2
(45) Date of Patent: Jul. 1, 2003

(54) PORTABLE LAMP HAVING BOTH A GERMICIDAL AND BLACK-GLASS LAMP TUBES

(76) Inventors: Jong-Jiing Shiau, 11F, No. 288-2, Ta-Ya Rd., Taichung (TW); Chi-Te Su, No. 102-14, Pei-Ping Rd., Sec. 2, Taichung (TW)

( * ) Notice: Subject to any disclaimer, the term of this patent is extended or adjusted under 35 U.S.C. 154(b) by 0 days.

(21) Appl. No.: 09/969,726

(22) Filed: Oct. 4, 2001

(65) Prior Publication Data

US 2003/0067768 A1 Apr. 10, 2003

(51) Int. Cl.$^7$ ................................................. F21V 9/00
(52) U.S. Cl. ....................... 362/231; 362/225; 362/241; 362/250; 362/371; 250/455.11; 250/461.1; 250/504 H
(58) Field of Search ................................. 362/225, 231, 362/241, 250, 371; 250/455.11, 461.1, 504 H

(56) References Cited

U.S. PATENT DOCUMENTS

| | | | | |
|---|---|---|---|---|
| 3,136,890 A | * | 6/1964 | Wein | 250/461.1 |
| 3,950,102 A | * | 4/1976 | Eickhorst | 362/231 |
| 4,287,554 A | * | 9/1981 | Wolff | 362/241 |
| 4,786,812 A | * | 11/1988 | Humphreys | 250/455.11 |
| 4,896,042 A | * | 1/1990 | Humphreys | 250/435 |
| 4,952,369 A | * | 8/1990 | Belilos | 362/157 |
| 5,788,364 A | * | 8/1998 | Cooper et al. | 362/373 |
| 5,920,075 A | * | 7/1999 | Whitehead | 250/492.1 |
| 6,005,254 A | * | 12/1999 | Wijtsma et al. | 250/493.1 |
| 6,242,753 B1 | * | 6/2001 | Sakurai | 250/455.11 |
| 6,280,048 B1 | * | 8/2001 | Luquire | 362/109 |

* cited by examiner

Primary Examiner—Sandra O'Shea
Assistant Examiner—Ismael Negron
(74) Attorney, Agent, or Firm—Birch, Stewart, Kolasch & Birch, LLP

(57) ABSTRACT

A portable dual lamp set consists of a base frame and a lamp casing mounted to the base frame for housing a germicidal lamp and a black-glass lamp. The base frame has a pedestal and a flange for fastening the lamp casing through an adjustment screw bolt and a screw nut to form an upright position or tilted at selected angles to suit different utilization. The lamp casing may also be detached for using separately. The lamp set provides dual effects for inspection and sterilization.

8 Claims, 7 Drawing Sheets

PORTABLE LAMP HAVING BOTH A GERMICIDAL AND BLACK-GLASS LAMP TUBES

FIELD OF THE INVENTION

The present invention relates to a lamp set and particularly a dual lamp set that has high portability for hand carrying or fixedly stationed at selected angles in different utilization conditions and provides dual effects for inspecting and sterilizing use.

BACKGROUND OF THE INVENTION

Black-glass lamps containing tricolor rare earth elements as fluorescent agents for examining and testing purposes are commonly used elements in test instruments. The black-glass lamps can emit invisible ultraviolet light (300–400 nm) which may be used to inspect stains on machinery, clothes, and skins, and to examine documents, gems and counterfeit currency, and to illuminate stages and billboards.

Conventional germicidal lamps emit invisible ultraviolet light (254 nm) to kill bacteria in a short time and do not generate foul smell. They mostly are used for medical treatments or cosmetic purposes, and have become an essential sterilizing instrument in people's daily life.

Presently, the foregoing two products are classified as technology products and have been used in many different areas. When in use, they usually have to couple with huge facilities. It is not convenient and is expensive, therefore is not suitable for general household use. They also rarely are owned and used at the same time. Hence their benefits have not been fully utilized and enjoyed. There are still rooms for improvement.

SUMMARY OF THE INVENTION

The primary object of the present invention is to provide a compact and portable dual lamp set that includes concurrently a black-glass lamp and a germicidal lamp to offer inspection and sterilization effects at the same time.

To attain the foregoing objects, the dual lamp set of the present invention mainly includes a base frame with a lamp casing mounted thereon. The lamp casing houses a germicidal lamp and a black-glass lamp. The base frame has a pedestal and a flange. Through adjusting and fastening screw bolts in a first and a second screw bores, the lamp casing may be erected upright or tilted to an angle desired to suit different using conditions. The lamp casing may also be detached from the base frame for use separately. The lamp set thus constructed can provide dual effects for inspecting and sterilizing.

The foregoing, as well as additional objects, features and advantages of the invention will be more readily apparent from the following detailed description, which proceeds with reference to the accompanying drawings.

DESCRIPTION OF THE PREFERRED EMBODIMENTS

Figure 1:
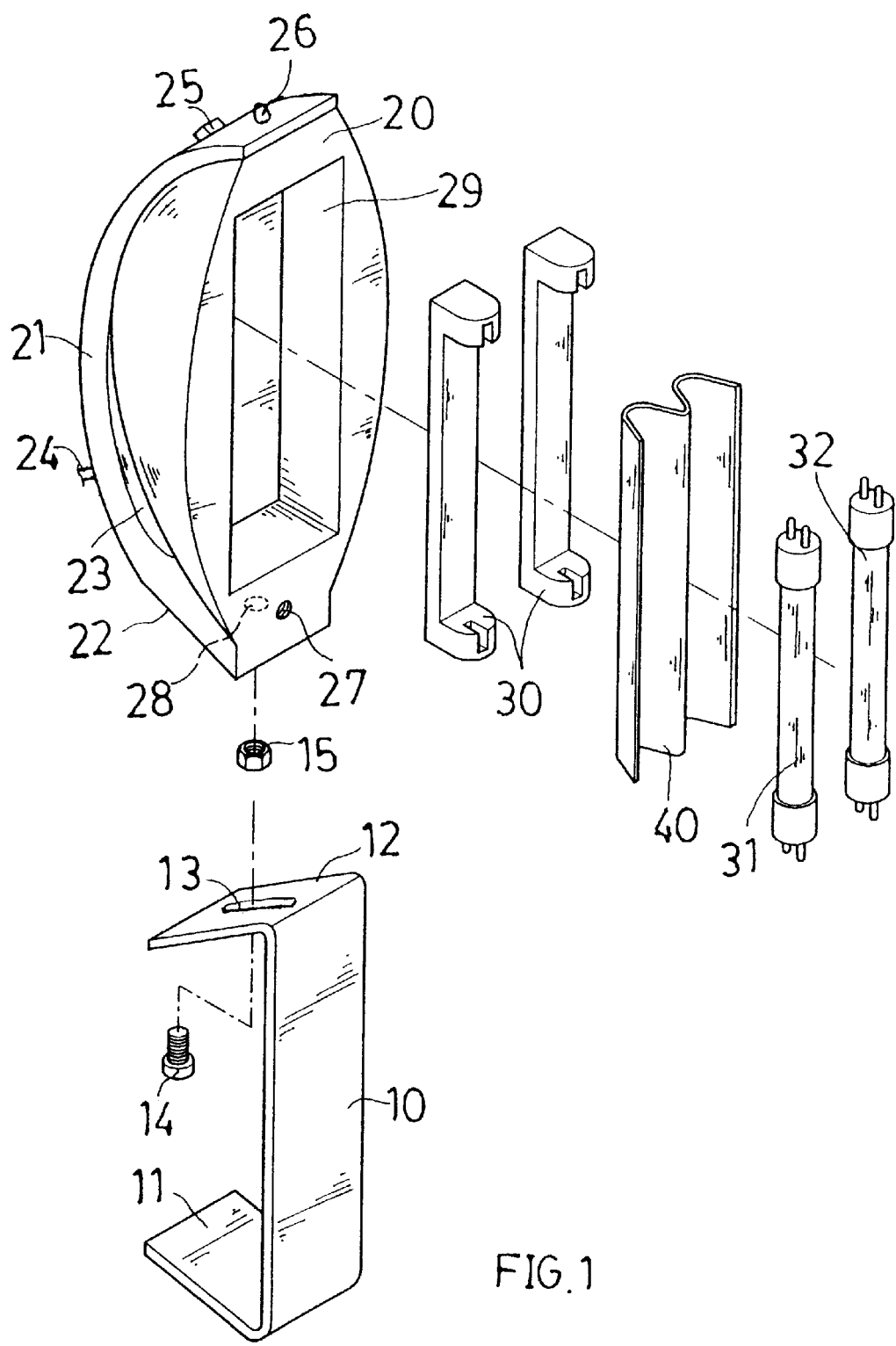
FIG. 1 is an exploded view of the invention.
Figure 4:
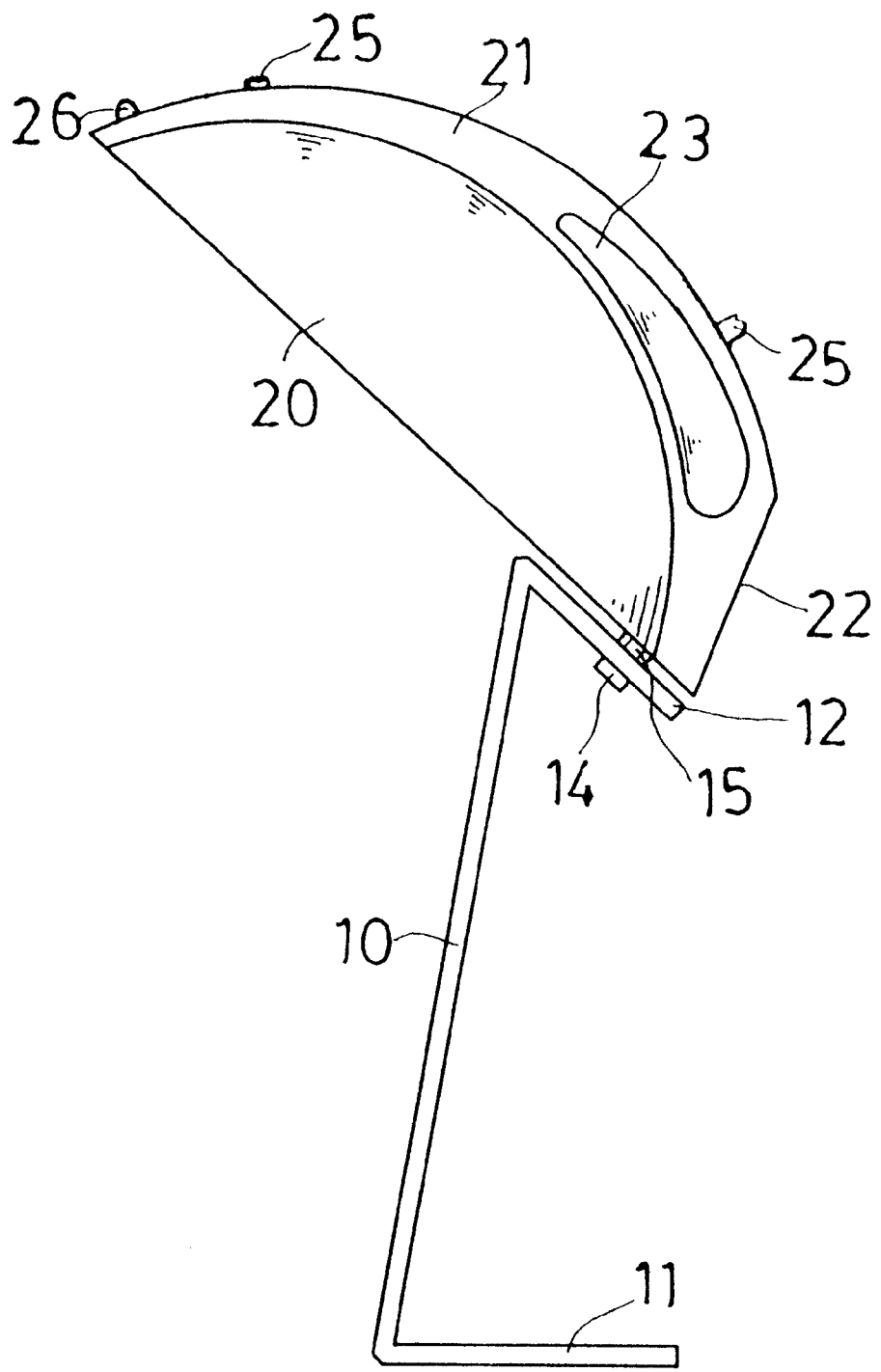
FIG. 4 is a side view of the invention, at yet another assembled configuration.

Referring to FIGS. 1 through 6, the invention mainly consists of:

a base frame 10 which is formed in a rectangular shape and includes a pedestal 11 located at the bottom and a flange 12 located at the top end and being bent and extended in a slant manner. The flange 12 has a slot 13 for engaging with an adjustment screw bolt 14 and a screw nut 15 with the screw nut 15 extending outside the screw bolt 14. The base frame 10 may be a transparent board or a colored transparent board;

a lamp casing 20 which may be mounted to the base frame 10 for use or held in the inner side of the base frame 10 and wedged between the pedestal 11 and flange 12 for storing (as shown in FIG. 4). The lamp casing 20 is formed in a size for hand holding by people. The lamp casing 20 is shaped substantially like a slice of a sphere with a jutting ridge 21 formed at the rear side for people to grasp with hands. The lamp casing 20 has a mounting section 22 formed at the bottom. The ridge 21 further has indented grooves 23 formed at two sides adjacent to the mounting section 22 to allow people grasping the ridge 21 securely and comfortably to conform ergonomic design. At the peripheral of the lamp casing 20, there is a power cord 24 linking to a three-way switch 25 and an indication light 26 for displaying power supply conditions. On the front side of the lamp casing 20 there is a first screw bore 27. On the mounting section 22, there is a second screw bore 28. In the front side of the lamp casing 20, there is a housing chamber 29;

two lamp brackets 30 located in the housing chamber 29 of the lamp casing 20 for mounting respectively a germicidal lamp 31 and a black-glass lamp 32; and a reflection hood 40 located between the lamp brackets 30 and the germicidal lamp 31 and black-glass lamp 32 to increase light intensity of the projecting light.

By means of the construction set forth above, the black-glass lamp 32 and the germicidal lamp 31 will generate respectively ultraviolet light of different wave lengths (300–400 nm, and 254 nm) to produce different effects desired. The black-glass lamp 32 may be used for detecting stains on machinery, clothes and skins, and for examining documents, gems, counterfeit currency or the like. The germicidal lamp 31 may be used for sterilization.

Figure 2:
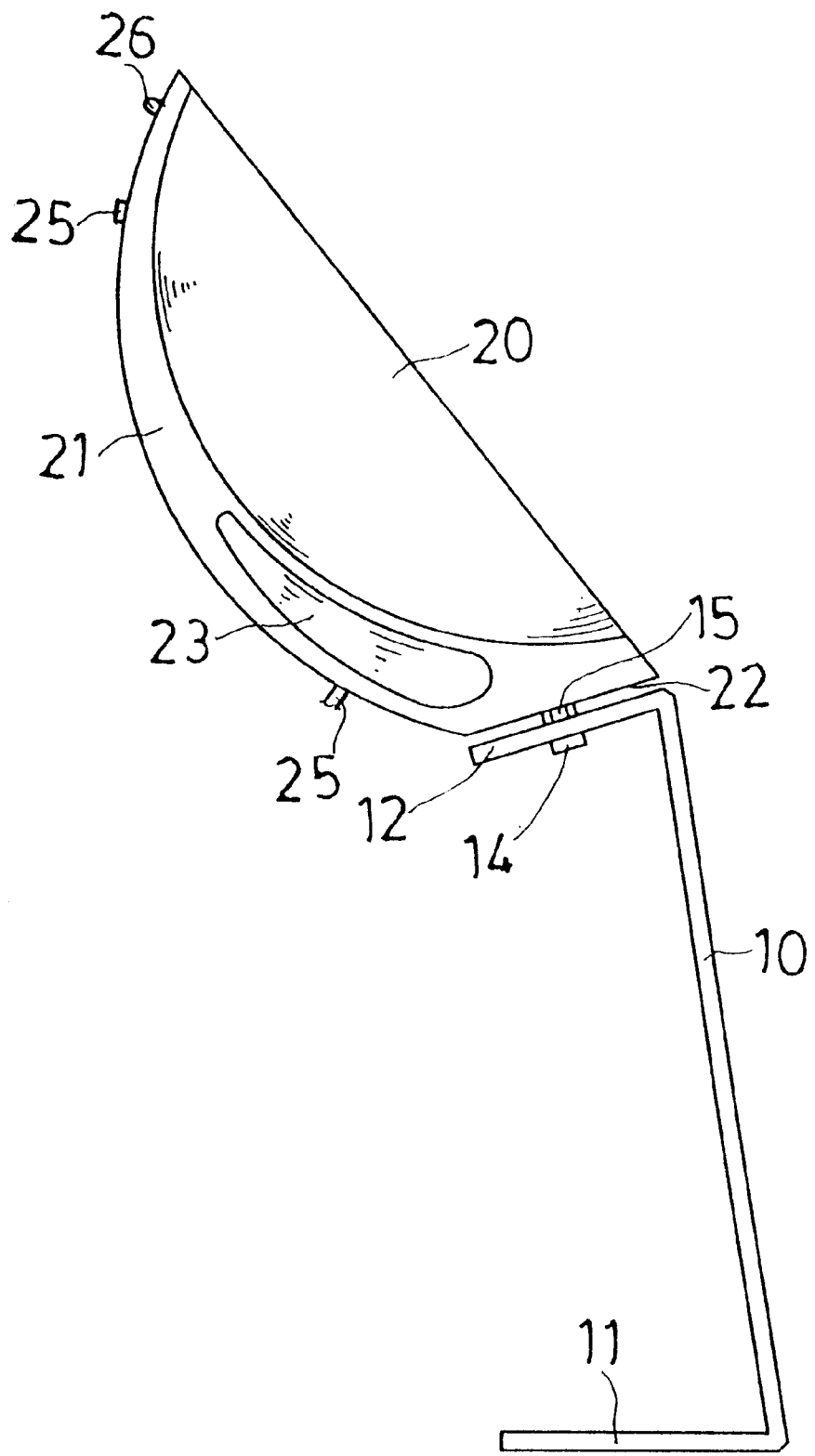
FIG. 2 is a side view of the invention, at one assembled configuration.

When in use, mount the lamp casing 20 to the flange 12 of the base frame 10, and use the adjustment screw bolt 14 to engage with the second screw bore 28 to erect the lamp casing 20 upright (as shown in FIG. 2). Activate the switch 25 to turn on the black-glass lamp 32, the ultraviolet light emitted by the black-glass lamp 32 may be used to examine skins. For instance, normal skin will become dark blue under the projection of the ultraviolet light. The skin having sunburn will have coffee color specks. The dry skin will look white or light blue. The oily skin will show orange and red colors. After the black-glass lamp 32 is turned off, the germicidal lamp 31 may be turned on through the switch 25. The ultraviolet light being generated may be used to constrain and retard the DNA of microbes, and to deprive their reproduction and breeding power. As exposing under the ultraviolet light for a prolonged period of time is harmful to human body, the present invention may include an automatic circuit to stop power supply in fifteen seconds after turn on. This will give users protection from negligent or indiscreet utilization.

Figure 3:
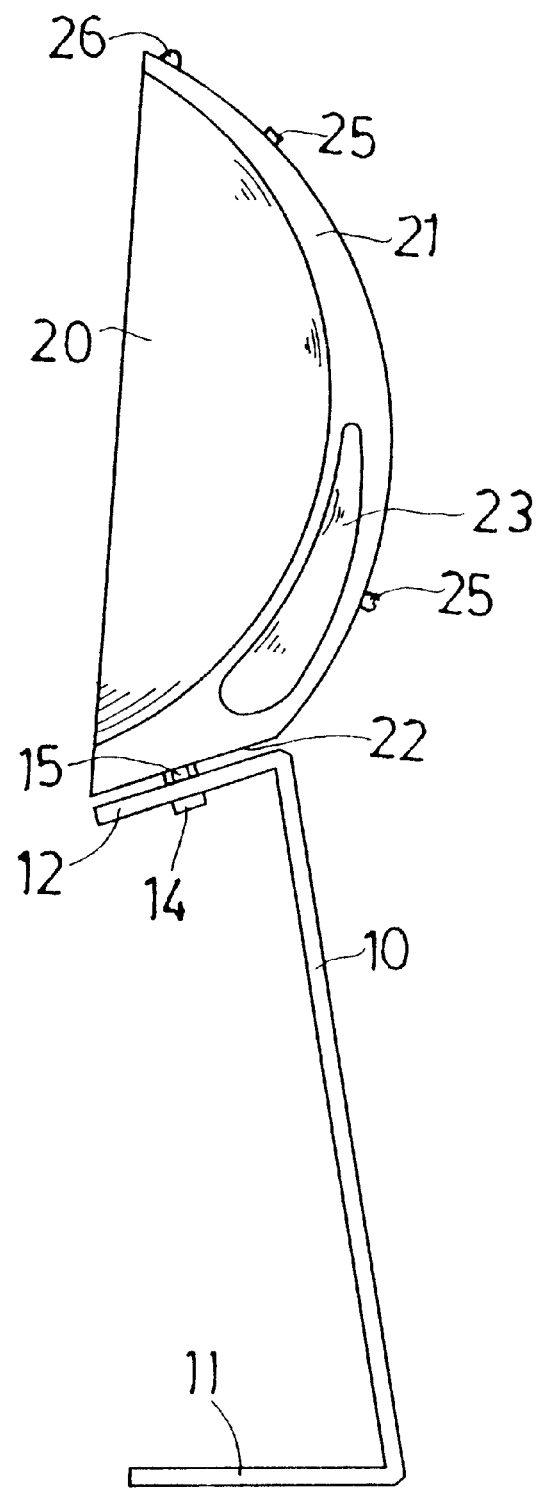
FIG. 3 is a side view of the invention, at another assembled configuration.

The lamp casing 20 may also be turned 180 degree (as shown in FIG. 3) with the lamp casing 20 mounting to the base frame 10 at another angle to suit users of different heights.

The slot 13 on the flange 12 also allows fine tuning adjustment of the lamp casing positions to suit different users' preference.

The lamp casing 20 may also be mounted to the flange 12 by fastening the adjustment screw bolt 14 to the first screw bore 27 (as shown in FIG. 4). In such a circumstance, the germicidal lamp 31 may be used for sterilization purpose, such as to project on foods, handkerchiefs, drinking water and the like. It is especially useful in the less developed areas where sanitary conditions are generally poor. It can greatly improve health and wellbeing of the people by sterilizing foods and water before consumption.

The base frame 10 and lamp casing 20 may also be separated. And the lamp casing 20 may be held by people's hands to project directly on articles for inspecting or sterilizing purpose.

Figure 5:
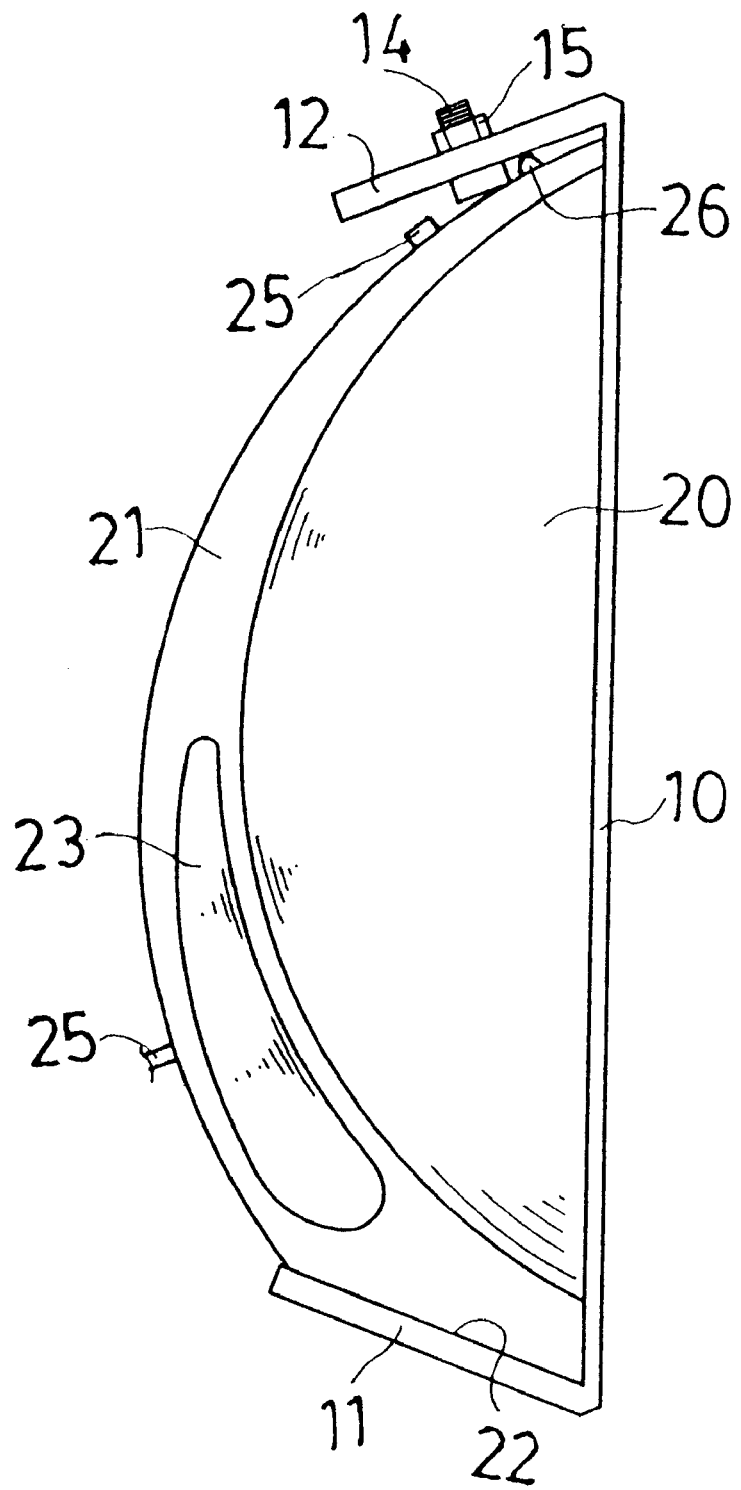
FIG. 5 is a schematic side view of the present invention, packed for storing.
Figure 6:
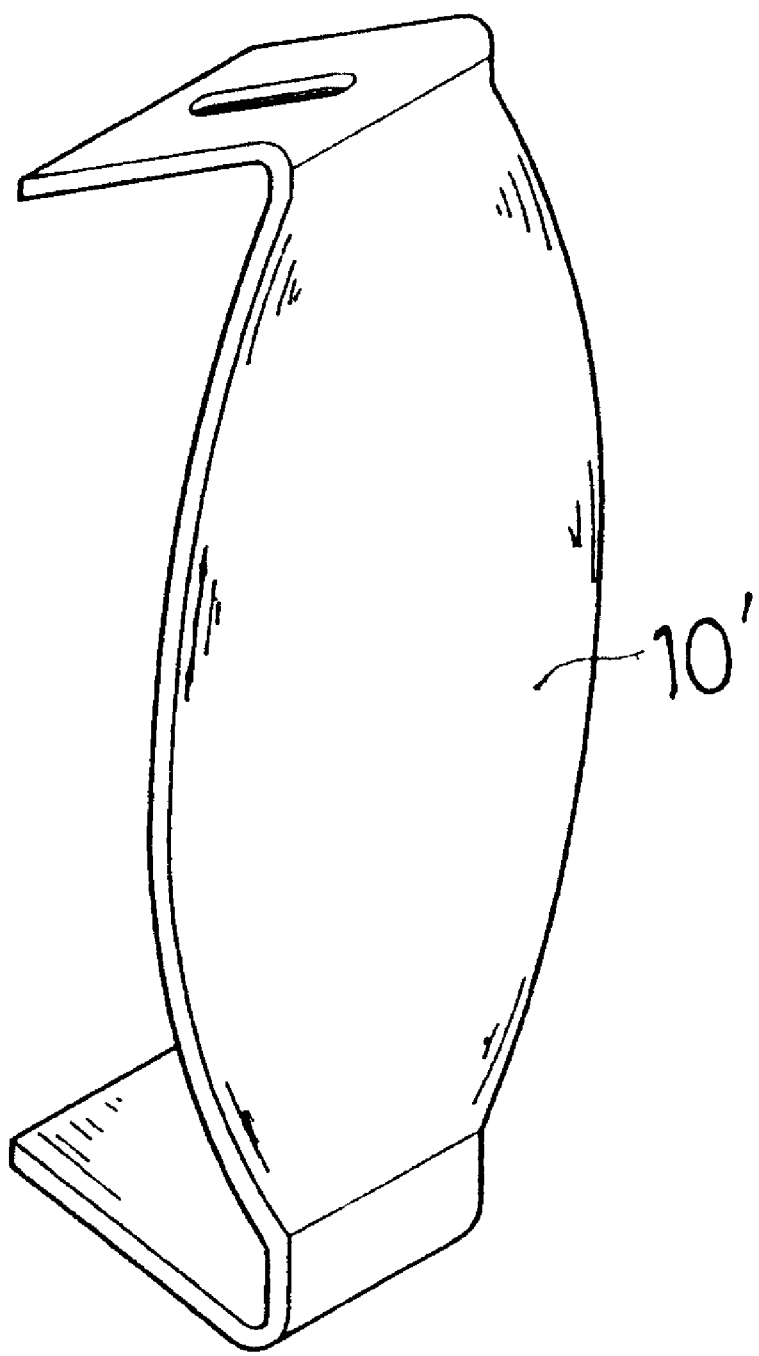
FIG. 6 is a perspective view of another embodiment of the base frame of the invention.

Furthermore, when not in use, loosen the adjustment screw bolt 14, the base frame 10 may be detached to encase the front side of the lamp casing 20 with the lamp casing 20 wedging between the flange 12 and pedestal 11 (as shown in FIG. 5) to form an integrated and compact size for storing. The front side of the base frame 10' may also be formed with a shape of a sphere segment (shown in FIG. 6) to completely cover the lamp casing 20 for storing.

Figure 7:
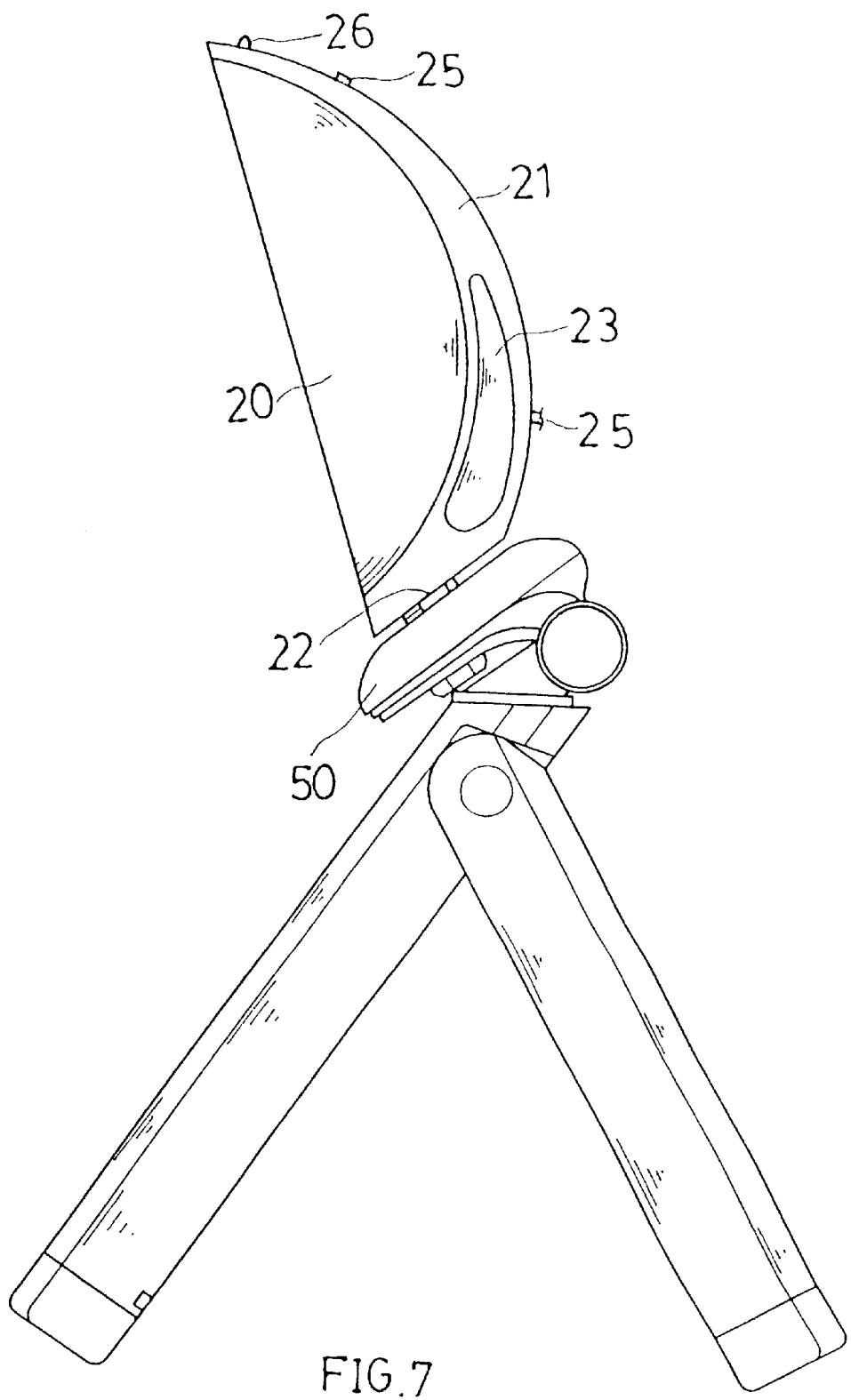
FIG. 7 is schematic view of the invention mounting to a tripod.

The invention may also be mounted to a tripod (50) that has been used in general video cameras, cameras, and telescopes (as shown in FIG. 7) to achieve the effects set forth above. As the tripod (50) is a very commonly used article, it may be used to adjust the height and angle of the invention freely and to make utilization of the invention even more convenient.

In summary, the invention has the following advantages:

1. The invention has a black-glass lamp and a germicidal lamp simultaneously, thus may provide dual effects for inspection and sterilization applications.
2. The invention is compact and portable, and may be used for skin cares anywhere and anytime with little restriction.
3. The invention is compact and portable, and may be used for sterilizing foods and articles anywhere and anytime.
4. The configuration of invention may be altered to suit various applications depending on requirements, such as detached for independent use, standing upright, or tilted an angle desired.
5. The invention may be fine tuned to various elevations and positions to suit different users' preference.

What is claimed is:

1. A portable dual lamp set comprising a base frame and a lamp casing mounted to the base frame for housing two lamp tubes, the base frame having a pedestal and a flange for fastening the lamp casing, the lamp tubes are respectively a germicidal lamp and a black-glass lamp.

2. The portable dual lamp set of claim 1, wherein the flange has a slot for engaging with an adjustment screw bolt and a screw nut with the screw nut extending outside the screw bolt.

3. The portable dual lamp set of claim 1, wherein the base frame is selectively a transparent board or a colored transparent board.

4. The portable dual lamp set of claim 1, wherein the lamp casing is sized for hand holding by people, and has two lamp tubes housed therein, and has a power cord, a switch and an indication light located on the peripheral rims thereof.

5. The portable dual lamp set of claim 1, wherein the lamp casing is shaped substantially in a section of a sphere with a jutting ridge formed on the rear side thereof, the ridge having indented grooves formed on, two sides thereof.

6. The portable dual lamp set of claim 1, wherein the lamp casing has a mounting section formed at the bottom side, and a first screw bore formed on the front side of the lamp casing and a second screw bore formed on the mounting section.

7. The portable dual lamp set of claim 1, wherein the lamp casing has two lamp brackets located therein for holding the lamp tubes.

8. The portable dual lamp set of claim 7, wherein the lamp casing has a reflection hood located between the lamp tubes for projecting light emitting from the lamp tubes to increase light intensity.

* * * * *